United States Patent [19]

Osborne

[11] Patent Number: 4,942,030
[45] Date of Patent: Jul. 17, 1990

[54] BIOLOGICAL CONTROL OF WHITEFLIES AND OTHER PESTS WITH A FUNGAL PATHOGEN

[75] Inventor: Lance S. Osborne, Altamonte Springs, Fla.

[73] Assignee: University of Florida Research Foundation, Incorporated, Alachua, Fla.

[21] Appl. No.: 155,332

[22] Filed: Feb. 12, 1988

[51] Int. Cl.⁵ .................... A01N 63/00; C12N 1/14; C12N 15/00
[52] U.S. Cl. ................... 424/93; 435/172.1; 435/254; 435/911
[58] Field of Search ............... 424/93; 435/911, 254, 435/172.1

[56] References Cited

U.S. PATENT DOCUMENTS 4,751,082   6/1988   Schaerffenberg et al. ........... 424/93

OTHER PUBLICATIONS

Chemical Abstracts, vol. 106, No. 1, Issued Jan. 1987, Abstract No. 2684g p. 261, Tech et al., *Trans. Br. Mycol Soc.* 1986 87(21215-222).

*Primary Examiner*—Richard A. Schwartz
*Assistant Examiner*—Richard C. Peet
*Attorney, Agent, or Firm*—Saliwanchik & Saliwanchik

[57] ABSTRACT

The subject invention concerns a novel biopesticide and its use to control whiteflies and other pests which cause a significant amount of damage to plants throughout the United States and the Caribbean. These pests are particularly destructive in greenhouses and nurseries. A virulent isolate of *Paecilomyces fumosoroseus* in an agricultural compositon, can be used to effectively control these insects. Exemplified herein is *Paecilomyces fumosoroseus* Apopka, ATCC 20874. By using this novel fungus, or mutants thereof, whiteflies and other pests can be controlled without the environmental and public safety hazards presented by chemical control agents.

15 Claims, No Drawings

BIOLOGICAL CONTROL OF WHITEFLIES AND OTHER PESTS WITH A FUNGAL PATHOGEN

BACKGROUND OF THE INVENTION

Whiteflies, mites, aphids, thrips, mealybugs, and other pests cause millions of dollars of damage each year to ornamental plants and plants grown in greenhouses. For example, the sweet potato whitefly *Bemisia tabaci* (Gennadius) has appeared on poinsettias in California, Florida, Georgia, and North Carolina. During 1981, *B. tabaci* was responsible for crop and market losses of $100 million in cotton, cucurbits, and lettuce in California and Arizona. The whitefly is increasingly a problem in Florida where, in 1986, *B. tabaci* caused approximately $2 million of damage to Florida's $8 to 10 million poinsettia crop.

*B. tabaci* is also a pest of international importance, having been found on host plants throughout the mideast Caribbean and Central America. This insect is now known to feed on more than 500 different plants, many of which are of importance in the Caribbean and Florida. For example, cassava, sweet potato, squash, tomato, beans, lettuce, cotton, pepper, carrot, cucumber, egg plant, and watermelon are all known hosts. This species of whitefly severely impacts infested plants by its feeding, production of honeydew with resultant growth of sooty mold, and transmission of plant pathogens. Most extensive losses to this pest have been through direct feeding damage and indirect damage through transmission of plant diseases.

Whitefly borne diseases are of major importance in tropical and subtropical agriculture. More than 70 diseases caused by viruses and microorganisms are known to be transmitted by whiteflies, with most of them being transmitted by *B. tabaci*. In Puerto Rico, this whitefly is a vector of at least seven diseases. One of these diseases is the bean golden mosaic virus, a disease affecting many legumes.

*B. tabaci* (Gennadius) has proven to be very difficult to control with conventional pesticide applications. Many factors contribute to the lack of control obtained with pesticides. The most important factor is that this whitefly has demonstrated a broad spectrum of resistance to chlorinated hydrocarbon, organophosphorus, carbamate, and synthetic pyrethroid insecticides. Very few commercially available pesticides are effective against whiteflies, and those which do work are only effective if care is taken to make a very thorough application of the insecticide several times a week. The sweet potato whitefly spends most of its life on the undersides of leaves, therefore, growers must adjust their management practices to permit increased pesticide coverage there. The spacing of the plants must be such that the chemical spray can penetrate the canopy and reach all surfaces of the plants.

In addition to being largely ineffective, and difficult and costly to apply, chemical control of these pests has other significant drawbacks. For example, the use of chemical pesticides presents the further disadvantages of polluting the environment, creating potential health hazards to agricultural workers and to consumers, development of resistance to chemicals in target pest species, detrimental effect of these chemicals on nontarget species resulting in secondary pest outbreaks, and phytotoxic reactions by treated plants.

Because of the problems associated with the use of chemical pesticides, safer and more effective methods of control for pests are clearly needed. Although biological control agents are actively being sought-after, to date no biological control agent has been commercially successful for the control of this whitefly.

Biological control agents are needed not only for *B. tabaci*, but also for other common pests of greenhouse and ornamental plants. These other common pest include mites, thrips, mealybugs, aphids, and scales. Twospotted spider mites, for example, feed on many species of plants and are a major pest of vegetables, ornamentals, fruit trees, hops, cotton, and strawberries. It is believed that widespread use of broad-spectrum insecticides destroy or greatly hamper natural enemies of spider mites and may thereby allow pest outbreaks to occur.

Biological control agents have been tried for many, if not all, of these pests. However, availability, limited host range, cost and reliability have reduced the potential for implementing the use of these biological control agents. The development of broad spectrum mycoinsecticides will reduce the need for many of the petrochemically based pesticides. By using fungi to control pests, the potential for resistance development is minimized, which, in turn, will stabilize many of the pest management programs.

BRIEF SUMMARY OF THE INVENTION

The subject invention concerns the use of a novel, highly virulent *Paecilomyces fumosoroseus* to control pests which attack ornamental plants and plants grown in greenhouses. Specifically exemplified herein is *P. fumosoroseus* Apopka. This fungus, advantageously, shows virulence against whiteflies, mites, aphids, thrips, mealybugs, and other pests. Also, the use of the claimed biological control agent does not produce the environmental hazards associated with chemical control agents. The fungus can be applied directly to the insects or it can be applied to the plants which are to be protected. The fungus can be used in greenhouses, nurseries, or any other place that whiteflies, mites, aphids, thrips, mealybugs, and other pests are a problem. The subject invention also includes mutants of *P. fumosoroseus* Apopka which substantially retain the virulence of the parent strain against nursery and greenhouse pests.

DETAILED DESCRIPTION OF THE INVENTION

A biologically pure culture of a novel isolate of *Paecilomyces fumosoroseus* of the subject invention, designated Apopka, has been deposited in the American Type Culture Collection (ATCC), 12301 Parklawn Drive, Rockville, MD 20852.

| Culture | Accession number | Deposit Date |
|---|---|---|
| *Paecilomyces fumosoroseus* Apopka | ATCC 20874 | February 4, 1988 |

The subject culture has been deposited under conditions that assure that access to the culture will be available during the pendency of the patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to furnish a sample when requested, due to the condition of the deposit. All restrictions on the availability to the public of the subject culture deposit will be irrevocably removed upon the granting of a patent disclosing it.

The taxonomic description of the novel isolate of *Paecilomyces fumosoroseus* claimed here is the same as that for other members of that species. See Samson (Samson, R. A. [1974] "Paecilomyces and some allied Hyphomyces," Stud. Mycol. 6: 1–116) for a taxonomic description of *P. fumosoroseus*. The novel isolate claimed here, *Paecilomyces fumosoroseus* Apopka, differs from other members of that species metabolically and biochemically in such a way that it is virulent against a number of important pests, as described below.

The novel fungus of the subject invention has been successfully grown on several different media including potato dextrose agar (PDA), V-8 TM juice agar, lima bean agar, oatmeal agar, and mixed cereal agar. Based on the diameter of the colonies, the spore production, and the cost and availability of the agars, Difco PDA TM and V-8 TM provide the best mediums for growing the fungus of the subject invention. Colonies on PDA are very fast growing with multinuclear colonies developing on the same plate shortly after the first sporulation occurs. A diameter of 4 cm. is obtained within 14 days at 24 C.

When whiteflies or other pests are exposed to *Paecilomyces fumosoroseus* the insects are killed when the fungus colonizes the insect. The fungus has been shown to colonize all life stages of the target insects thereby facilitating immediate and long-term control of the pests. Table 1 shows the results of experiments accessing the fungus' ability to infect the pupae of *B. tabaci*. The treatment group involved in these experiments was treated with *Paecilomyces fumosoroseus* Apopka at a concentration of $1 \times 10^6$ spores/ml. The control group was not treated with the fungus and were dipped in a 1.2 g/500 ml CAPTAN TM (Orthocide) solution to kill all contaminants.

TABLE 1

| Infection rate of 50 papae of *B. tabaci* after treatment with $1 \times 10^6$ spores/ml solution of *Paecilomyces fumosoroseus* Apopka. | | |
|---|---|---|
| | % infection | |
| Days post-treatment | control | treatment |
| 3 | 0 | 64 |
| 5 | 0 | 76 |
| 6 | 0 | 82 |
| 7 | 0 | 86 |

Results of experiments assessing the fungus' ability to colonize the larvae of 2 species of whitefly—*Bemisia tabaci* (sweet potato whitefly) and *Dialeurodes citri* (citrus whitefly)—are shown in Table 2.

TABLE 2

| Colonization of Sweet Potato Whitefly, *Bemisia tabaci* and Citrus Whitefly, *Dialeurodes citri* by the novel fungus *Paecilomyces fumosoroseus* Apopka. | | |
|---|---|---|
| Concentration (# spores/ml) colonized | % of *Bemisia tabaci* colonized | % of *Dialeurodes citri* |
| none | 0 | 0 |
| $1 \times 10^6$ | 39 | 27 |
| $5 \times 10^6$ | 41 | 38 |
| $1 \times 10^7$ | 73 | 50 |

In addition to whiteflies, the fungus claimed here has also been observed to have activity against *Thrips tabaci* (onion thrips), *Spodopter littoralis*, *Spodoptera xigua* (beet army worm), *Leptinotarsa decemlineata* (Colorado potato beetle), *Lymantria dispar* (Gypsy moth), *Tetranychus urticae* (Twospotted spider mite), *Franliniella* (flower thrips), *Echinothrips americanus*, *Planococcus citri* (Citrus mealybug), and *Phenaococcus solani* (Solanum mealybug).

Advantageously, the fungus of the claimed invention is not adversely affected by most chemical control agents. As Table 3 shows, very few of the commonly used chemical control agents show activity against the fungus. This means that the fungus can be used before, after, or in conjunction with chemical control agents. The chemical pesticides listed in Table 3 are all trade names known to persons in the pesticide art.

TABLE 3

| Activity of common chemical pesticides against the fungus *Paecilomyces fumosoroseus*. | |
|---|---|
| Chemical pesticide | Activity against *P. fumosoroseus* Apopka |
| Aliette 80% WP | NO |
| Avid | NO |
| Bayleton 25% WP | NO |
| Benlate 50% WP | NO |
| Botran 75W | NO |
| Carbamate 76% | NO |
| Chipco 26019 (50 WP) | NO |
| Cyprex 65% WP | NO |
| Daconil 2787 75% WP | NO |
| Dursban 50W | NO |
| Flutolanil | NO |
| Kocide 101 (77%) | NO |
| Lesan (35%) | NO |
| Manzate 200 (80%) WP | YES |
| Ornalin 50 WP | NO |
| Orthocide 50W | YES |
| Orthene | NO |
| Prochloraz | YES |
| Spotless | NO |
| Subdue 2E | NO |
| Sufers Insecticidal Soap | NO |
| Sulfur | NO |
| Talstan 10 WP | NO |
| Terraclor 75% WP | NO |
| Terraguard | YES |
| Truban 30% WP | NO |
| Vitavax | NO |
| Vydate 2L | NO |
| Zineb | NO |
| Zyban 75% WP | NO |

Spraying is the preferred method of applying the fungus of the claimed invention. The fungus may be applied to insects directly, to the foliage of plants, or the surroundings. A fungal suspension containing from about $1 \times 10^5$ to about $1 \times 10^9$ spores per milliliter of water and 2 drops of TWEEN TM per liter can be sprayed either on the insect or on the plants which are to be protected. The TWEEN™ acts as a wetting agent and other equivalent wetting agents can be used. In order to prepare the fungus for application, the spores can be harvested from a culture by pouring 0.05% TRITON™ in the petri dish and then diluting with sterile deionized water.

The fungus may also be applied in conjunction with a powder or granular carrier. As with spray application, the powder or granular formulation may be applied directly to the insect, the foliage of the plants, or the surroundings. To prepare the fungus for mixing with the powder or granular carrier it may be scraped or otherwise removed from the surface of the growth medium and combined with rice or any other granular or powder material which does not inhibit the growth of the fungus. Although the fungus may be applied in conjunction with a granular carrier, application may be easier and more uniform if the carrier and fungus mixture has a powder consistency. If necessary to achieve a particle size appropriate for easy application, the fungus/particle mixture may be slowly ground until the desired consistency is achieved. This means of formulation results in the application of a mixture which comprises fungal spores and mycelia together with a carrier. The presence of both the spores and the mycelia facilitates rapid and widespread colonization of the target insects. The application of the fungus and powder carrier can be accomplished using an aerosol applicator.

I claim:

1. A *Paecilomyces fumosoroseus* which, when in its essentially biologically pure form, has the virulence against whiteflies characteristic of *Paecilomyces fumosoroseus* Apopka, culture deposit ATCC 20874.

2. A composition for controlling a pest selected from the group consisting of *Bemisia tabaci, Dialeurodes citri, Thrips tabaci, Spodoptera littoralis, Spodoptera xigua, Leptinotarsa decemlineata, Lymantria dispar, Tetranychus urticae, Frankliniella, Echinothrips americanus, Planococcus citri,* and *Phenaococcus solani,* said composition comprising a *Paecilomyces fumosoroseus* which, when in its essentially biologically pure form, has the identifying characteristics of *Paecilomyces fumosoroseus* Apopka, culture deposit ATCC 20874, in association with an agricultural carrier.

3. A composition, according to claim 2, wherein the agricultural carrier is a liquid, a powder, granules, or small particles.

4. A composition, according to claim 3, wherein the liquid comprises water and a wetting agent.

5. A composition, according to claim 2, wherein the agricultural carrier comprises rice or ground-up rice.

6. A composition, according to claim 2, wherein said agricultural carrier is liquid and said *Paecilomyces fumosoroseus* is in the spore form at a concentration of from about $1 \times 10^5$ spores/ml carrier to about $1 \times 10^9$ spores/ml of carrier.

7. A process for controlling a pest selected from the group consisting of *Bemisia tabaci, Dialeurodes citri, Thrips tabaci, Spodoptera littoralis, Spodoptera xigua, Lepinotarsa decemlineata, Lymantria dispar, Tetranychus urticae, Frankliniella, Echinothrips americanus, Planococcus citri,* and *Phenaococcus solani,* said process comprising applying a *Paecilomyces fumosoroseus* which, when in its essentially biologically pure form, has the identifying characteristics of *Paecilomyces fumosoroseus* Apopka, culture deposit ATCC 20874, onto said pests, the foliage of plants, or the soil around plants.

8. The process, according to claim 7, wherein said fungus is applied, along with a liquid carrier, directly to individual plants or small groups of pests.

9. A process, according to claim 7, wherein said fungus is applied, along with a liquid carrier, directly to the foliage of plants.

10. A process, according to claim 7, wherein said fungus is applied, along with a powder, small particles, or granular carrier, to the soil around plants.

11. A process, according to claim 7, wherein said fungus is used to control whiteflies.

12. A process, according to claim 7, wherein the target pests are mealybugs.

13. A process, according to claim 7, wherein the target pests are of the order Diptera.

14. A process, according to claim 7, wherein the target pests are of the order Hymenoptera.

15. A process, according to claim 7, wherein the target pests are of the order Lepidoptera.

* * * * *